(12) United States Patent
Yamaguchi et al.

(10) Patent No.: US 6,620,601 B1
(45) Date of Patent: Sep. 16, 2003

(54) METHODS FOR TRANSFORMATION OF PLANTS, TRANSFORMED PLANTS AND PROCESSES FOR PREPARATION OF POLYESTERS

(75) Inventors: Isamu Yamaguchi, Saitama (JP); Hideo Nakashita, Tokyo (JP); Keiko Yoshioka, Osaka (JP); Yoshiharu Doi, Saitama (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 09/635,132

(22) Filed: Aug. 9, 2000

(30) Foreign Application Priority Data

Aug. 9, 1999 (JP) ............................................ 11-225832
Aug. 9, 1999 (JP) ............................................ 11-225839

(51) Int. Cl.[7] .............................. C12P 1/00; C12P 7/62; C12N 15/82; C12N 5/04; C12N 5/10
(52) U.S. Cl. ........................ 435/135; 435/41; 435/468; 435/419; 800/295; 800/298
(58) Field of Search .......................... 435/41, 135, 468, 435/419; 800/295, 298

(56) References Cited

U.S. PATENT DOCUMENTS 5,530,191 A * 6/1996 Maliga
6,117,658 A * 9/2000 Dennis et al.
6,143,561 A * 11/2000 Randall et al.

FOREIGN PATENT DOCUMENTS

| WO | 92/19747 | 11/1992 |
| WO | 95/05472 | 2/1995 |
| WO | 98/00557 | 1/1998 |
| WO | 98/04713 | 2/1998 |

OTHER PUBLICATIONS

Watson et al. Molecular Biology Of The Gene vol. I General Principles.*
Svab et al (1993) Proc. Natl. Aci. USA 90:913–917.*
Itaya (1999) J. Bacteriolgy 181:2045–1048.*
Song et al (1992) Korean J. Genet. 14:51–59, abstract only provided.*
Toshiaki Fukui et al., "Cloning and Analysis of the Poly(3–Hydroxybutyrate–co–3–Hydroxyhexanoate) Biosynthesis Genes of *Aeromonas caviae*.", Journal of Bacteriology, vol. 179, No. 15, pp. 4821–4830, Aug. 1997, Polymer Chemistry Laboratory, Institute of Physical and Chemical Research (RIKEN), Hirosawa, Wako–shi, Saitama 351–01, Japan, XP–002113257.
Henry E. Valentin et al., "PHA production, from bacteria to plants.", International Journal of Biological Macromolecules., vol. 25, No. 1–03, pp. 303–306, (1999), Monsanto Company, Agricultural Sector, 700 Chesterfield parkway North, St. Louis, Missouri 63198, XP–000892982.

* cited by examiner

Primary Examiner—James Ketter
Assistant Examiner—Konstantina Katcheves
(74) Attorney, Agent, or Firm—Foley & Lardner

(57) ABSTRACT

The present invention relates to a method for the transformation of a plant characterized by ligating an operon to a vector, the operon containing a promoter and 2–100 genes of interest, and integrating the resulting recombinant vector into a plastid chromosome, to a transformed plant obtained by the method, and the a process for preparing a polyester characterized by culturing or cultivating the transformed plant and collecting the polyester from the cultured or cultivated plant.

26 Claims, 6 Drawing Sheets

Prrn: 16S rRNA promoter
aadA: Aminoglycoside-3-adenyltransferase
psbA 3': psbA 3' regulatory region rbcL: Tobacco plastid gene
ORF512: Tobacco plastid gene aadA: Aminoglycoside-3-adenyltransferase (spectinomycin-, streptomycin-resistant)
phbC: Poly-3-hydroxybutyrate synthase
phbA: β-ketothiolase
phbB: Acetoacetyl-CoA reductase aadA: Aminoglycoside-3-adenyltransferase (spectinomycin-, streptomycin-resistant)
phbC: Poly-3-hydroxybutyrate synthase
phbA: β-ketothiolase
phbB: Acetoacetyl-CoA reductase

SEQUENCE LISTING

<160> NUMBER OF SEQ ID NOS: 18

<210> SEQ ID NO 1
<211> LENGTH: 4984
<212> TYPE: DNA
<213> ORGANISM: Ralstonia eutropha

<400> SEQUENCE: 1

```
cccgggcaag taccttgccg acatctatgc gctggcgcgc acgcgcctgg cgcgcgccgg      60
ctgtaccgag gtctacggcg gcgacgcctg caccgtggcc gacgccggtc gcttctactc     120
ctatcggcgc gatggcgtga ccggccgcat ggccagcctg gtctggctgg cggactgagc     180
ccgccgctgc ctcactcgtc cttgccctg gccgcctgcg cgcgctcggc ttcagccttg      240
cgtcggcggc ggccgggcgt gcccatgatg tagagcacca cgccaccggc gccatgccat     300
acatcaggaa ggtggcaacg cctgccacca cgttgtgctc ggtgatcgcc atcatcagcg     360
ccacgtagag ccagccaatg gccacgatgt acatcaaaaa ttcatccttc tcgcctatgc     420 tctgggcct cggcagatgc gagcgctgca taccgtccgg taggtcggga agcgtgcagt      480
gccgaggcgg attcccgcat tgacagcgcg tgcgttgcaa ggcaacaatg gactcaaatg     540
tctcggaatc gctgacgatt cccaggtttc tccggcaagc atagcgcatg gcgtctccat     600
gcgagaatgt cgcgcttgcc ggataaaagg ggagccgcta tcggaatgga cgcaagccac     660
ggccgcagca ggtgcggtcg agggcttcca gccagttcca gggcagatgt gccggcagac     720
cctcccgctt tgggggaggc gcaagccggg tccattcgga tagcatctcc ccatgcaaag     780
tgccggccag ggcaatgccc ggagccggtt cgaatagtga cggcagagag acaatcaaat     840
catggcgacc ggcaaaggcg cggcagcttc cacgcaggaa ggcaagtccc aaccattcaa     900
ggtcacgccg gggccattcg atccagccac atggctggaa tggtcccgcc agtggcaggg     960
cactgaaggc aacggccacg cggccgcgtc cggcattccg ggcctggatg cgctggcagg    1020
cgtcaagatc gcgccggcgc agctgggtga tatccagcag cgctacatga aggacttctc    1080
agcgctgtgg caggccatgg ccgagggcaa ggccgaggcc accggtccgc tgcacgaccg    1140
gcgcttcgcc ggcgacgcat ggcgcaccaa cctcccatat cgcttcgctg ccgcgttcta    1200
cctgctcaat gcgcgcgcct tgaccgagct ggccgatgcc gtcgaggccg atgccaagac    1260
```

-continued

```
ccgccagcgc atccgcttcg cgatctcgca atgggtcgat cgatgtcgc ccgccaactt    1320
ccttgccacc aatcccgagg cgcagcgcct gctgatcgag tcgggcggcg aatcgctgcg    1380
tgccggcgtg cgcaacatga tggaagacct gacacgcggc aagatctcgc agaccgacga    1440
gagcgcgttt gaggtcggcc gcaatgtcgc ggtgaccgaa ggcgccgtgg tcttcgagaa    1500
cgagtacttc cagctgttgc agtacaagcc gctgaccgac aaggtgcacg cgcgcccgct    1560
gctgatggtg ccgccgtgca tcaacaagta ctacatcctg gacctgcagc cggagagctc    1620
gctggtgcgc catgtggtgg agcagggaca tacggtgttt ctggtgtcgt ggcgcaatcc    1680
ggacgccagc atggccggca gcacctggga cgactacatc gagcacgcgg ccatccgcgc    1740
catcgaagtc gcgcgcgaca tcagcggcca ggacaagatc aacgtgctcg gcttctgcgt    1800
gggcggcacc attgtctcga ccgcgctggc ggtgctggcc gcgcgcggcg agcacccggc    1860
cgccagcgtc acgctgctga ccacgctgct ggactttgcc gacacgggca tcctcgacgt    1920
ctttgtcgac gagggccatg tgcagttgcg cgaggccacg ctgggcggcg cgccggcgc    1980
gccgtgcgcg ctgctgcgcg ccttgagct ggccaatacc ttctcgttct tgcgcccgaa    2040
cgacctggtg tggaactacg tggtcgacaa ctacctgaag gcaacacgc cggtgccgtt    2100
cgacctgctg ttctggaacg cgacgccac caacctgccg gggccgtggt actgctggta    2160
cctgcgccac acctacctgc agaacgagct caaggtaccg ggcaagctga ccgtgtgcgg    2220
cgtgccggtc gacctggcca gcatcgacgt gccgacctat atctacggct cgcgcgaaga    2280
ccatatcgtg ccgtggaccg cggcctatgc ctcgaccgcg ctgctggcga caagctgcg    2340
cttcgtgctg ggtgcgtcgg gccatatcgc cggtgtgatc aacccgccgg ccaagaacaa    2400
gcgcagccac tggactaacg atgcgctgcc ggagtcgccg cagcaatggc tggccggcgc    2460
catcgagcat cacggcagct ggtggccgga ctggaccgca tggctggccg ggcaggccgg    2520
cgcgaaacgc gccgcgcccg ccaactatgg caatgcgcgc tatcgcgcaa tcgaacccgc    2580
gcctgggcga tacgtcaaag ccaaggcatg acgcttgcat gagtgccggc gtgcgtcatg    2640
cacggcgccg gcaggcctgc aggttccctc ccgtttccat tgaaaggact acacaatgac    2700
tgacgttgtc atcgtatccg ccgcccgcac cgcggtcggc aagtttggcg gctcgctggc    2760
caagatcccg gcaccggaac tgggtgccgt ggtcatcaag gccgcgctgg agcgcgccgg    2820
cgtcaagccg gagcaggtga gcgaagtcat catgggccag gtgctgaccg ccggttcggg    2880
ccagaacccc gcacgccagg ccgcgatcaa ggccggcctg ccggcgatgg tgccggccat    2940
gaccatcaac aaggtgtgcg cgctcgggcct gaaggccgtg atgctggccg ccaacgcgat    3000
catggcgggc gacgccgaga tcgtggtggc cggcggccag gaaaacatga gcgccgcccc    3060
gcacgtgctg ccgggctcgc gcgatggttt ccgcatgggc gatgccaagc tggtcgacac    3120
catgatcgtc gacggcctgt gggacgtgta caaccagtac cacatgggca tcaccgccga    3180
gaacgtggcc aaggaatacg gcatcacacg cgaggcgcag gatgagttcg ccgtcggctc    3240
gcagaacaag gccgaagccg cgcagaaggc cggcaagttt gacgaagaga tcgtcccggt    3300
gctgatcccg cagcgcaagg cgacccggt ggccttcaag accgacgagt tcgtgcgcca    3360
gggcgccacg ctggacagca tgtccggcct caagcccgcc ttcgacaagg ccggcacggt    3420
gaccgcggcc aacgcctcgg gcctgaacga cggcgccgcc gcggtggtgg tgatgtcggc    3480
ggccaaggca aaggaactgg gcctgacccc gctggccacg atcaagagct atgccaacgc    3540
cggtgtcgat cccaaggtga tgggcatggg cccggtgccg gcctccaagc gcgccctgtc    3600
```

-continued

| | |
|---|---|
| gcgcgccgag tggaccccgc aagacctgga cctgatggag atcaacgagg cctttgccgc | 3660 |
| gcaggcgctg gcggtgcacc agcagatggg ctgggacacc tccaaggtca atgtgaacgg | 3720 |
| cggcgccatc gccatcggcc acccgatcgg cgcgtcgggc tgccgtatcc tggtgacgct | 3780 |
| gctgcacgag atgaagcgcc gtgacgcgaa gaagggcctg gcctcgctgt gcatcggcgg | 3840 |
| cggcatgggc gtggcgctgg cagtcgagcg caaataagga aggggttttc cggggccgcg | 3900 |
| cgcggttggc gcggacccgg cgacgataac gaagccaatc aaggagtgga catgactcag | 3960 |
| cgcattgcgt atgtgaccgg cggcatgggt ggtatcggaa ccgccatttg ccagcggctg | 4020 |
| gccaaggatg gctttcgtgt ggtggccggt tgcggcccca actcgccgcg ccgcgaaaag | 4080 |
| tggctggagc agcagaaggc cctgggcttc gatttcattg cctcggaagg caatgtggct | 4140 |
| gactgggact cgaccaagac cgcattcgac aaggtcaagt ccgaggtcgg cgaggttgat | 4200 |
| gtgctgatca caacgccgg tatcacccgc gacgtggtgt tccgcaagat gacccgcgcc | 4260 |
| gactgggatg cggtgatcga caccaacctg acctcgctgt tcaacgtcac caagcaggtg | 4320 |
| atcgacggca tggccgaccg tggctggggc cgcatcgtca acatctcgtc ggtgaacggg | 4380 |
| cagaagggcc agttcggcca gaccaactac tccaccgcca aggccggcct gcatggcttc | 4440 |
| accatggcac tggcgcagga agtggcgacc aagggcgtga ccgtcaacac ggtctctccg | 4500 |
| ggctatatcg ccaccgacat ggtcaaggcg atccgccagg acgtgctcga caagatcgtc | 4560 |
| gcgacgatcc cggtcaagcg cctgggcctg ccggaagaga tcgcctcgat ctgcgcctgg | 4620 |
| ttgtcgtcgg aggagtccgg tttctcgacc ggcgccgact tctcgctcaa cggcggcctg | 4680 |
| catatgggct gacctgccgg cctggttcaa ccagtcggca gccggcgctg gcgcccgcgt | 4740 |
| attgcggtgc agccagcgcg gcgcacaagg cggcgggcgt ttcgtttcgc cgcccgtttc | 4800 |
| gcgggccgtc aaggcccgcg aatcgtttct gcccgcgcgg cattcctcgc tttttgcgcc | 4860 |
| aattcaccgg gttttcctta agccccgtcg cttttcttag tgccttgttg ggcatagaat | 4920 |
| cagggcagcg gcgcagccag caccatgttc gtgcagcgcg ccctcgcgg gggcgaggct | 4980 |
| gcag | 4984 |

<210> SEQ ID NO 2
<211> LENGTH: 1770
<212> TYPE: DNA
<213> ORGANISM: Ralstonia eutropha

<400> SEQUENCE: 2

| | |
|---|---|
| atggcgaccg gcaaaggcgc ggcagcttcc acgcaggaag gcaagtccca accattcaag | 60 |
| gtcacgccgg ggccattcga tccagccaca tggctggaat ggtcccgcca gtggcagggc | 120 |
| actgaaggca acgccacgc ggccgcgtcc ggcattccgg gcctggatgc gctggcaggc | 180 |
| gtcaagatcg cgccggcgca gctgggtgat atccagcagc gctacatgaa ggacttctca | 240 |
| gcgctgtggc aggccatggc cgagggcaag gccgaggcca ccggtccgct gcacgaccgg | 300 |
| cgcttcgccg cgacgcatg cgcaccaac ctcccatatc gcttcgctgc cgcgttctac | 360 |
| ctgctcaatg cgcgcgcctt gaccgagctg gccgatgccg tcgaggccga tgccaagacc | 420 |
| cgccagcgca tccgcttcgc gatctcgcaa tgggtcgatg cgatgtcgcc cgccaacttc | 480 |
| cttgccacca atcccgaggc gcagcgcctg ctgatcgagt cgggcggcga atcgctgcgt | 540 |
| gccgcgtgc gcaacatgat ggaagacctg acacgcggca agatctcgca gaccgacgag | 600 |
| agcgcgtttg aggtcggccg caatgtcgcg gtgaccgaag cgccgtggt cttcgagaac | 660 |
| gagtacttcc agctgttgca gtacaagccg ctgaccgaca aggtgcacgc gcgcccgctg | 720 |

```
ctgatggtgc cgccgtgcat caacaagtac tacatcctgg acctgcagcc ggagagctcg      780
ctggtgcgcc atgtggtgga gcagggacat acggtgtttc tggtgtcgtg gcgcaatccg      840
gacgccagca tggccggcag cacctgggac gactacatcg agcacgcggc catccgcgcc      900
atcgaagtcg cgcgcgacat cagcggccag gacaagatca cgtgctcgg cttctgcgtg       960 ggcggcacca ttgtctcgac cgcgctggcg gtgctggccg cgcgcggcga gcacccggcc     1020
gccagcgtca cgctgctgac cacgctgctg gactttgccg acacgggcat cctcgacgtc     1080
tttgtcgacg agggccatgt gcagttcgcg gaggccacgc tgggcggcgg cgccggcgcg     1140
ccgtgcgcgc tgctgcgcgg ccttgagctg gccaatacct tctcgttctt gcgcccgaac     1200
gacctggtgt ggaactacgt ggtcgacaac tacctgaagg gcaacacgcc ggtgccgttc     1260
gacctgctgt tctggaacgg cgacgccacc aacctgccgg gccgtggta ctgctggtac      1320 ctgcgccaca cctacctgca gaacgagctc aaggtaccgg gcaagctgac cgtgtgcggc     1380
gtgccggtgg acctggccag catcgacgtg ccgacctata tctacggctc gcgcgaagac     1440
catatcgtgc cgtggaccgc ggcctatgcc tcgaccgcgc tgctggcgaa caagctgcgc     1500
ttcgtgctgg gtgcgtcggg ccatatcgcc ggtgtgatca acccgccggc caagaacaag     1560
cgcagccact ggactaacga tgcgctgccg gagtcgccgc agcaatggct ggccggcgcc     1620
atcgagcatc acggcagctg gtggccggac tggaccgcat ggctggccgg gcaggccggc     1680
gcgaaacgcg ccgcgcccgc caactatggc aatgcgcgct atcgcgcaat cgaacccgcg     1740
cctgggcgat acgtcaaagc caaggcatga                                      1770

<210> SEQ ID NO 3
<211> LENGTH: 1181
<212> TYPE: DNA
<213> ORGANISM: Ralstonia eutropha

<400> SEQUENCE: 3
tgactgacgt tgtcatcgta tccgccgccc gcaccgcggt cggcaagttt ggcggctcgc       60
tggccaagat cccggcaccg gaactgggtg ccgtggtcat caaggccgcg ctggagcgcg      120
ccggcgtcaa gccggagcag gtgagcgaag tcatcatggg ccaggtgctg accgccggtt      180
cgggccagaa ccccgcacgc caggccgcga tcaaggccgg cctgccggcg atggtgccgg      240
ccatgaccat caacaaggtg tgcggctcgg gcctgaaggc cgtgatgctg gccgccaacg      300
cgatcatggc gggcgacgcc gagatcgtgg tggccggcgg ccaggaaaac atgagcgccg      360
ccccgcacgt gctgccgggc tcgcgcgatg gtttccgcat gggcgatgcc aagctggtcg      420
acaccatgat cgtcgacggc ctgtgggacg tgtacaacca gtaccacatg ggcatcaccg      480
ccgagaacgt ggccaaggaa tacggcatca cacgcgaggc gcaggatgag ttcgccgtcg      540
gctcgcagaa caaggccgaa gccgcgcaga aggccggcaa gtttgacgaa gagatcgtcc      600
cggtgctgat cccgcagcgc aagggcgacc cggtggcctt caagaccgac gagttcgtgc      660
gccagggcgc cacgctggac agcatgtccg gcctcaagcc cgccttcgac aaggccggca      720
cggtgaccgc ggccaacgcc tcgggcctga cgacggcgc cgccgcggtg gtggtgatgt      780
cggcggccaa ggcaaggaa ctgggcctga ccccgctggc cacgatcaag agctatgcca      840
acgccggtgt cgatcccaag gtgatgggca tgggcccggt gccggcctcc aagcgcgccc      900
tgtcgcgcgc cgagtggacc ccgcaagacc tggacctgat ggagatcaac gaggcctttg      960
ccgcgcaggc gctggcggtg caccagcaga tgggctggga cacctccaag gtcaatgtga     1020
```

-continued

```
acggcggcgc catcgccatc ggccacccga tcggcgcgtc gggctgccgt atcctggtga    1080
cgctgctgca cgagatgaag cgccgtgacg cgaagaaggg cctggcctcg ctgtgcatcg    1140
gcggcggcat gggcgtggcg ctggcagtcg agcgcaaata a                        1181
```

<210> SEQ ID NO 4
<211> LENGTH: 741
<212> TYPE: DNA
<213> ORGANISM: Ralstonia eutropha

<400> SEQUENCE: 4

```
atgactcagc gcattgcgta tgtgaccggc ggcatgggtg gtatcggaac cgccatttgc      60
cagcggctgg ccaaggatgg cttcgtgtg gtggccggtt gcggccccaa ctcgccgcgc     120
cgcgaaaagt ggctggagca gcagaaggcc ctgggcttcg atttcattgc ctcggaaggc    180
aatgtggctg actgggactc gaccaagacc gcattcgaca aggtcaagtc cgaggtcggc    240
gaggttgatg tgctgatcaa caacgccggt atcacccgcg acgtggtgtt ccgcaagatg    300
acccgcgccg actgggatgc ggtgatcgac accaacctga cctcgctgtt caacgtcacc    360
aagcaggtga tcgacggcat ggccgaccgt ggctggggcc gcatcgtcaa catctcgtcg    420
gtgaacgggc agaagggcca gttcggccag accaactact ccaccgccaa ggccggcctg    480
catggcttca ccatggcact ggcgcaggaa gtggcgacca agggcgtgac cgtcaacacg    540
gtctctccgg gctatatcgc caccgacatg gtcaaggcga tccgccagga cgtgctcgac    600
aagatcgtcg cgacgatccc ggtcaagcgc ctgggcctgc cggaagagat cgcctcgatc    660
tgcgcctggt tgtcgtcgga ggagtccggt ttctcgaccg cgccgacttc tcgctcaac    720 ggcggcctgc atatgggctg a                                              741
```

<210> SEQ ID NO 5
<211> LENGTH: 795
<212> TYPE: DNA
<213> ORGANISM: Escherichia coli

<400> SEQUENCE: 5

```
atggctagtg aagcggttat cgccgaagta tcaactcaac tatcagaggt agttggcgtc      60
atcgagcgcc atctcgaacc gacgttgctg gccgtacatt tgtacggctc cgcagtggat    120
ggcggcctga agccacacag tgatattgat ttgctggtta cggtgaccgt aaggcttgat    180
gaaacaacgc ggcgagcttt gatcaacgac cttttggaaa cttcggcttc ccctggagag    240
agcgagattc tccgcgctgt agaagtcacc attgttgtgc acgacgacat cattccgtgg    300
cgttatccag ctaagcgcga actgcaattt ggagaatggc agcgcaatga cattcttgca    360
ggtatcttcg agccagccac gatcgacatt gatctggcta tcttgctgac aaaagcaaga    420
gaacatagcg ttgccttggt aggtccagcg cggaggaac tctttgatcc ggttcctgaa     480
caggatctat ttgaggcgct aaatgaaacc ttaacgctat ggaactcgcc gcccgactgg    540
gctggcgatg agcgaaatgt agtgcttacg ttgtcccgca tttggtacag cgcagtaacc    600
ggcaaaatcg cgccgaagga tgtcgctgcc gactgggcaa tggagcgcct gccggcccag    660
tatcagcccg tcatacttga agctagacag gcttatcttg acaagaaga agatcgcttg    720 gcctcgcgcg cagatcagtt ggaagaattt gtccactacg tgaaaggcga gatcactaag    780
gtagtcggca aataa                                                     795
```

<210> SEQ ID NO 6
<211> LENGTH: 30

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
tctggatcca tggctagtga agcggttatc                                        30

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
ttgagatcta gactgcagtt atttgccgac taccttgg                               38

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
atggatcccg ggcaagtacc ttgccgacat                                        30

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
tccggatcct atgcccaaca aggcactaag a                                      31

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
atcggatcca gggagggaat catggcgacc ggcaaaggcg cg                          42

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
agcaagcttt tcaatggaaa cgggagggaa cctg                                   34

<210> SEQ ID NO 12
<211> LENGTH: 40
<212> TYPE: DNA
```

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: Synthetic DNA

<400> SEQUENCE: 12
atcaagctta gggagggaac aatgactgac gttgtcatcg                          40

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Synthetic DNA

<400> SEQUENCE: 13
agagaattcc cttgattggc ttcgttatcg tcgc                                34

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Synthetic DNA

<400> SEQUENCE: 14
atcgaattca gggagggaac atgactcagc gcattgcgta tgtg                     44

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic DNA

<400> SEQUENCE: 15
agaggatccc aggccggcag gtcagcccat atgc                                34

<210> SEQ ID NO 16
<211> LENGTH: 127
<212> TYPE: DNA
<213> ORGANISM: Nicotiana tabacum

<400> SEQUENCE: 16
ctagttggat tgctcccccc gccgtcgttc aatgagaatg gataagaggc tcgtgggatt    60
gacgtgaggg ggcagggatg gctatatttc tgggagcgaa ctccgggcga atatgaagcg   120
catggat                                                             127

<210> SEQ ID NO 17
<211> LENGTH: 388
<212> TYPE: DNA
<213> ORGANISM: Nicotiana tabacum

<400> SEQUENCE: 17
ctggcctagt ctataggagg ttttgaaaag aaaggagcaa taatcatttt cttgttctat    60
caagagggtg ctattgctcc tttctttttt tctttttatt tatttactag tatttttactt  120 acatagactt ttttgtttac attatagaaa agaaggagag ggttattttc ttgcatttat   180
tcatgattga gtattctatt ttgattttgt atttgtttaa attgtgaaat agaacttgtt   240
tctcttcttg ctaatgttac tatatctttt tgatttttt tttccaaaaa aaaaatcaaa    300

```
ttttgacttc ttcttatctc ttatctttga atatctctta tctttgaaat aataatatca    360
ttgaaataag aaagaagagc tatattcg                                        388

<210> SEQ ID NO 18
<211> LENGTH: 4260
<212> TYPE: DNA
<213> ORGANISM: Nicotiana tabacum

<400> SEQUENCE: 18
aaaaattggg ttgcgctata tatatgaaag agtatacaat aatgatgtat ttggcaaatc     60
aaataccatg gtctaataat caaacattct gattagttga taatattagt attagttgga    120
aattttgtga aagattccta tgaaaagttt cattaacacg gaattcgtgt cgagtagacc    180
ttgttgttgt gagaattctt aattcatgag ttgtagggag ggatttatgt caccacaaac    240
agagactaaa gcaagtgttg gattcaaagc tggtgttaaa gagtacaaat tgacttatta    300
tactcctgag taccaaacca aggatactga tatattggca gcattccgag taactcctca    360
acctggagtt ccacctgaag aagcaggggc cgcggtagct gccgaatctt ctactggtac    420
atggacaact gtatggaccg atggacttac cagccttgat cgttacaaag gcgatgcta     480 ccgcatcgag cgtgttgttg gagaaaaaga tcaatatatt gcttatgtag cttacccttt    540 agacctttt gaagaaggtt ctgttaccaa catgtttact tccattgtag gtaacgtatt     600
tgggttcaaa gccctgcgcg ctctacgtct ggaagatctg cgaatccctc ctgcttatgt    660
taaaactttc caaggtccgc tcatgggat ccaagttgaa agagataaat tgaacaagta     720
tggtcgtccc ctgttgggat gtactattaa acctaaattg gggttatctg ctaaaaacta    780
cggtagagcc gtttatgaat gtcttcgcgg tggacttgat tttactaaag atgatgagaa    840
cgtgaactca caaccattta tgcgttggag agatcgtttc ttattttgtg ccgaagcact    900
ttataaagca caggctgaaa caggtgaaat caaagggcat tacttgaatg ctactgcagg    960
tacatgcgaa gaaatgatca aaagagctgt atttgctaga gaattgggcg ttccgatcgt   1020
aatgcatgac tacttaacgg ggggattcac cgcaaatact agcttggctc attattgccg   1080
agataatggt ctacttcttc acatccaccg tgcaatgcat gcggttattg atagacagaa   1140
gaatcatggt atccacttcc gggtattagc aaaagcgtta cgtatgtctg gtggagatca   1200
tattcactct ggtaccgtag taggtaaact tgaaggtgaa agagacataa ctttgggctt   1260
tgttgattta ctgcgtgatg attttgttga acaagatcga agtcgcggta tttatttcac   1320
tcaagattgg gtctctttac caggtgttct acccgtggct tcaggaggta ttcacgtttg   1380
gcatatgcct gctctgaccg agatctttgg ggatgattcc gtactacagt tcggtggagg   1440
aactttagga catccttggg gtaatgcgcc aggtgccgta gctaatcgag tagctctaga   1500
agcatgtgta aaagctcgta atgaaggacg tgatcttgct caggaaggta atgaaattat   1560
tcgcgaggct tgcaaatgga gcccggaact agctgctgct tgtgaagtat ggaaagagat   1620
cgtatttaat tttgcagcag tggacgtttt ggataagtaa aaacagtaga cattagcaga   1680
taaattagca ggaaataaag aaggataagg agaagaact caagtaatta tccttcgttc    1740
tcttaattga attgcaatta aactcggccc aatcttttac taaaaggatt gagccgaata   1800
caacaaagat tctattgcat atattttgac taagtatata cttacctaga tatacaagat   1860
ttgaaataca aaatctagaa aactaaatca aatctaaga ctcaaatctt tctattgttg    1920
tcttggatcc acaattaatc ctacggatcc ttaggattgg tatattcttt tctatcctgt   1980
```

-continued

| | |
|---|---|
| agtttgtagt ttccctgaat caagccaagt atcacacctc tttctaccca tcctgtatat | 2040 |
| tgtccccttt gttccgtgtt gaaatagaac cttaatttat tacttatttt tttattaaat | 2100 |
| tttagatttg ttagtgatta gatattagta ttagacgaga ttttacgaaa caattatttt | 2160 |
| tttatttctt tataggagag gacaaatctc ttttttcgat gcgaatttga cacgacatag | 2220 |
| gagaagccgc cctttattaa aaattatatt attttaaata atataaaggg ggttccaaca | 2280 |
| tattaatata tagtgaagtg ttcccccaga ttcagaactt ttttttcaata ctcacaatcc | 2340 |
| ttattagtta ataatcctag tgattggatt tctatgctta gtctgatagg aaataagata | 2400 |
| ttcaaataaa taattttata gcgaatgact attcatctat tgtattttca tgcaaatagg | 2460 |
| gggcaagaaa actctatgga aagatggtgg tttaattcga tgttgtttaa gaaggagttc | 2520 |
| gaacgcaggt gtgggctaaa taaatcaatg ggcagtcttg gtcctattga aaataccaat | 2580 |
| gaagatccaa atcgaaaagt gaaaaacatt catagttgga ggaatcgtga caattctagt | 2640 |
| tgcagtaatg ttgattattt attcggcgtt aaagacattc ggaatttcat ctctgatgac | 2700 |
| acttttttag ttagtgatag gaatgggac agttattcca tctattttga tattgaaaat | 2760 |
| catattttg agattgacaa cgatcattct tttctgagtg aactagaaag ttcttttttat | 2820 |
| agttatcgaa actcgaatta tcggaataat ggatttaggg gcgaagatcc ctactataat | 2880 |
| tcttacatgt atgatactca atatagttgg aataatcaca ttaatagttg cattgatagt | 2940 |
| tatcttcagt ctcaaatctg tatagatact tccattataa gtggtagtga gaattacggt | 3000 |
| gacagttaca tttatagggc cgtttgtggt ggtgaaagtc gaaatagtag tgaaaacgag | 3060 |
| ggttccagta gacgaactcg cacgaagggc agtgatttaa ctataagaga aagttctaat | 3120 |
| gatctcgagg taactcaaaa atacaggcat ttgtgggttc aatgcgaaaa ttgttatgga | 3180 |
| ttaaattata agaatttttt gaatcaaaa atgaatattt gtgaacaatg tggatatcat | 3240 |
| ttgaaaatga gtagttcaga tagaattgaa cttttgatcg atccgggtac ttgggatcct | 3300 |
| atggatgaag acatggtctc tctagatccc attgaatttc attcggagga ggagccttat | 3360 |
| aaagatcgta ttgattctta tcaaagaaag acaggattaa ccgaggctgt tcaaacaggc | 3420 |
| ataggccaac taaacggcat tcccgtagca attggggtta tggattttca gtttatgggg | 3480 |
| ggtagtatgg gatccgtagt cggagagaaa atcacccgtt tgattgaata cgctgccaat | 3540 |
| caaattttac cccttattat agtgtgtgct tctgggggg cgcgcatgca ggaaggaagt | 3600 |
| ttgagcttga tgcaaatggc taaaatatcg tctgctttat atgattatca attaaataaa | 3660 |
| aagttatttt atgtatcaat ccttacatct ccgacaactg gtggagtgac agctagtttt | 3720 |
| ggtatgttgg gggatatcat tattgccgaa cccaacgcct acattgcatt tgcaggtaaa | 3780 |
| agagtaattg aacaaacatt gaataaaaca gtacccgaag gttcacaagc agctgaatac | 3840 |
| ttattccaga agggtttatt cgacctaatt gtaccacgta atcttttaaa aagcgttctg | 3900 |
| agtgagttat ttaagctcca cgccttttt cctttgaatc aaaagtcaag caaaatcaag | 3960 |
| tagagcacta agttcaatta ttttatttgt gtttgtagca aaaagtagt tagtttgtcg | 4020 |
| gaatcaaagt aaataagata ataatggcgc tttctttggt gatagaagat ctaattgtag | 4080 |
| aaagaatcaa aactaaagtt gaggataact ctttttttga cctatattcc tgattacgaa | 4140 |
| tcaagaagcc tttatcaaca agagtgagtt cttcctttcg tgaaattagg aaaataaaac | 4200 |
| gaatttcttc ttcttgtctt aggtatataa tttgaaattc aaatatagat aatagagttt | 4260 |

METHODS FOR TRANSFORMATION OF PLANTS, TRANSFORMED PLANTS AND PROCESSES FOR PREPARATION OF POLYESTERS

TECHNICAL FIELD

The present invention relates to a method for transforming plants, to transformed plants obtained by this method, to a process for preparing polyesters characterized by culturing or cultivating the transformed plants and subsequently collecting the polyesters from the cultured or cultivated plants.

BACKGROUND OF THE INVENTION

It is known that in eukaryotes the gene expression is controlled by promoter and terminator which exist every distinct gene and that poly A sequence is added to 3'-terminus of MRNA generated by transcription. Because the gene expression occurs within nucleus, any try to produce a plant with new trait using transformation methods for plants has been carried out predominantly by methods comprising introducing a gene into the nucleus chromosome.

However, genes of eukaryotes are monocistronic; that is, one gene is controlled by a single promoter. In prokaryotic cells which have the polycistronic expression mechanism where multiple genes are controlled by only one promoter, when a prokaryotic gene is transferred to the nucleus chromosome of a eukaryote then it is necessary to ligate a promoter to each gene. This procedure is thus complicated.

By the way, polyesters, such as poly-3-hydroxyalkanoic acids, that are biosynthesized by microorganisms have thermoplastic properties and are wide variety of biodegradable plastics from rigid ones to rubber-like ones having viscoelasticity.

Recently, the binary copolymer polyester P(3HB-co-3HH) of 3-hydroxybutyrate (3HB) and 3-hydroxyhexanoate (3HH) as well as its production methods have been studied and developed (e.g., see JP-A-5-93049 and JP-A-7-265065). The methods for the preparation of the copolymer P(3HB-co-3HH) as disclosed therein are based on its production from oleic acid or olive oil by fermentation using *Aeromonas caviae* isolated from soil. The copolymer, which is produced by fermentation process for the purpose of energy storage, becomes a material of flexible polymers because the crystallinity of the copolymer is decreased as the unit fraction of 3HH is increased. Hence, it has good thermostability and molding properties and can be processed into strong yarn and flexible films (Y. Doi, S. Kitamura, and H. Abe, Macromolecules 28, 4822–4823 (1995)). Additionally, because polyesters produced by microorganisms are biodegradable, they are useful in view of the protection of environment. Thus polyesters, which are produced and accumulated in microorganisms, may have wide variety of applications.

However, when polyesters are produced in microorganisms then certain installations including culture apparatus and medium would be needed. Further, when the installations are run, production costs are raised since the petroleum energy is consumed. Under these circumstances, there are demands for development of means of preparing polyesters, which have the above-mentioned properties, economically in large amounts without use of microbial culture means.

The object of the present invention is to provide a method for transformation of plants, transformed plants obtained by this method, and a process for preparing a polyester characterized by culturing or cultivating the transformed plant and subsequently collecting the polyester from the cultured or cultivated plant.

SUMMARY OF THE INVENTION

The present inventor studied intensively to solve the above-described problems. As a result, the inventor succeeded in obtaining a polyester by integrating an operon that has multiple genes including polyester synthase gene into the plastid of a plant to transform the plant in which polycistronic gene expression is possible even in eukarote like plant, culturing or cultivating the obtained transformed plant, and collecting the polyester from the cultured or cultivated plant, whereby the present invention was accomplished.

The present invention provides a method for the transformation of a plant wherein the method comprises ligating an operon to a vector, the operon containing a promoter and 2–100 genes of interest, and integrating the resulting recombinant vector into the plastid chromosome of a plant. The present invention also provides a transformed plant in which the said operon is integrated into the plastid chromosome. In the invention, for example, the said 2 genes of interest are a polyester synthase gene and a gene different from the polyester synthase gene; and the said 3 genes of interest are a polyester synthase gene, β-ketothiolase gene, and acetoacetyl-CoA reductase gene.

The present invention further provides a process for preparing a polyester wherein the process comprises integrating a recombinant vector to which an operon containing a promoter, a polyester synthase gene and 1–100 genes different from the polyester synthase gene is ligated, into a plastid chromosome of a plant to transform the plant, culturing or cultivating the obtained transformed plant, and collecting the polyester from the cultured or cultivated plant.

Example of the polyester synthase gene is a poly-3-hydroxybutyrate synthase gene. As the plant, exemplified are transformed plants belonging to any family selected from the group consisting of Solanaceae (e.g. *Nicotiana tabacum*), Gramineae, Malvaceae, Brassicaceae, Compositae, Pedaliaceae, Oleaceae, Myrtaceae, Rosaceae, Theaceae, Leguminosae, palmae, Sterculiaceae, and Rubiaceae.

Example of the polyester includes a copolymer of 3-hydroxyalkanoic acid represented by the following formula I:

$$\text{HO}-\overset{\overset{\displaystyle R}{|}}{\text{CH}}-\text{CH}_2-\text{COOH} \tag{I}$$

wherein R represents a hydrogen atom or a $C_{1-4}$ alkyl group.

DETAILED DESCRIPTION OF THE INVENTION

Figure 1:
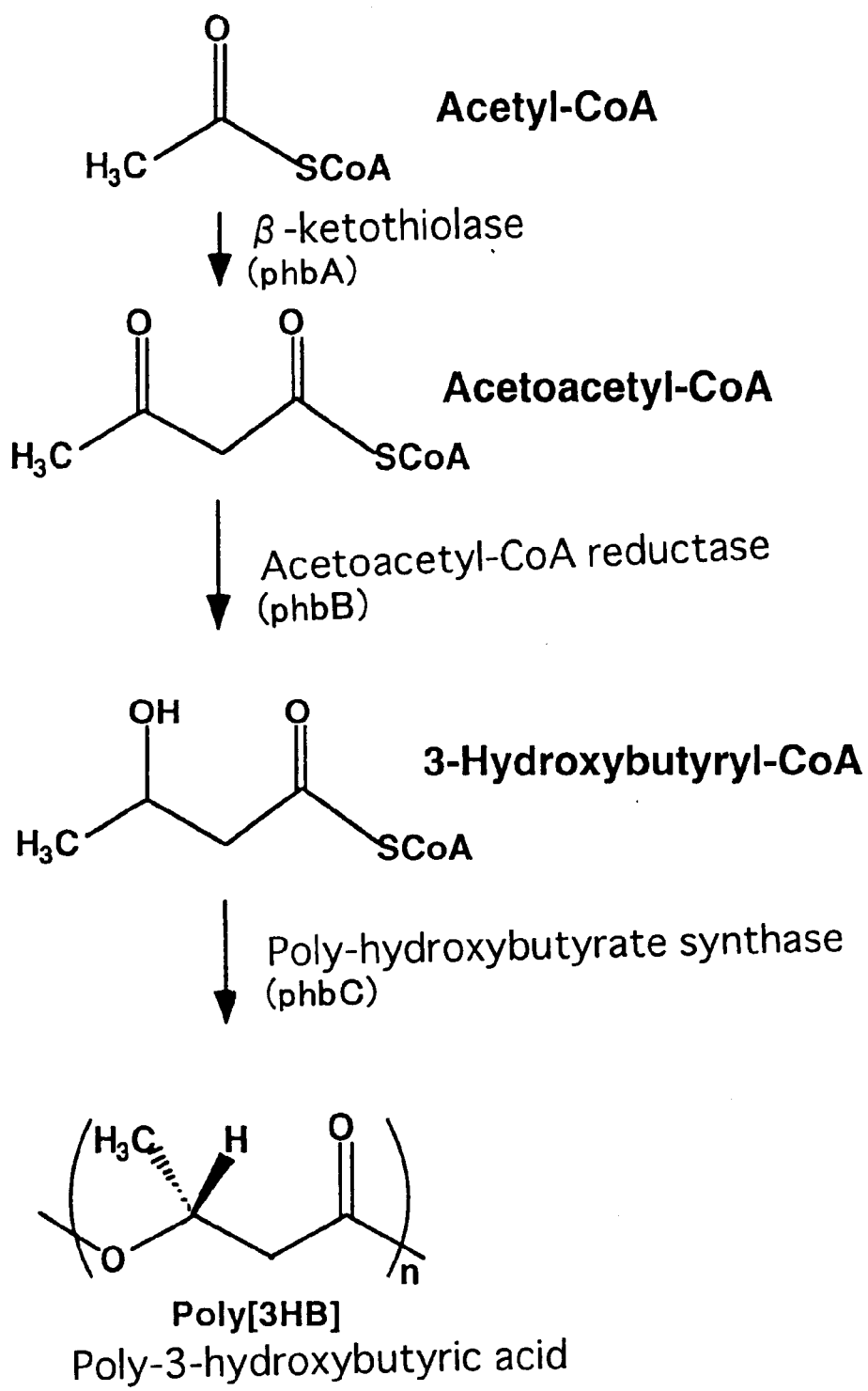
FIG. 1 shows the reaction pathway from acetyl-CoA to polyester formation.

The present invention will be described in detail hereinafter.

The present invention is characterized in that an operon which comprises a plurality of (i.e., 2–100 kinds of) genes and a promoter is inserted into a vector to obtain a recombinant vector which is then introduced into the plastid chromosome of a plant thereby transforming the plant. The present invention is also characterized by such a transformed plant and by culturing or cultivating the transformed plant and collecting a polyester from the cultured or cultivated plant.

As used herein, the term "plastid" refers to a DNA-containing organelle unique to plant cells. In plants, proplastid changes to structures carrying a variety of functions (e.g., photosynthesis, synthesis of amino acids and fatty acids, nitrogen fixation, etc.), such as leukoplast, etioplast, chloroplast, chromoplast, amyloplast, and elaioplast. These structures are designated plastid.

In cells of eukaryotes, the plastid including chloroplast is a major, unique organelle in plant cell and serves for photosynthetic reaction. The plastid and mitochondria, which are involved in metabolism of energy, have distinct chromosomes from that present in nucleus and are replicable autonomously.

The factor σ which functions in the plastid is coded by nucleus chromosome and is one of transcriptional factors which transfer to the plastid following expression. The presence of the bacterial-type factor σ is also known.

Furthermore, the fact that plastid genes are controlled in a similar way to that in bacteria has been clarified by studies on transcriptional mechanism of genes. Thus, the structure and expression manner of a chromosomal gene of the plastid are similar to those of a prokaryotic gene; that is, multiple genes are linked in series to form an operon. The genes present on the plastid operon are controlled by a single promoter, and all the genes are transcribed concurrently to generate a mRNA strand.

Thus the chromosomal genes in plastid are controlled by the similar mechanism to that of bacteria. In the present invention, when the metabolic system useful in microorganisms, like production of materials or decomposition of less degradable substances, is introduced into a plant, a group of genes is introduced as a prokaryotic cell type structure into a plastid. This procedure is different from the prior one designed so that each gene is expressed in a eukaryotic cell. The transformation method accomplished by the present inventor has benefits of a simple operation and a good efficiency. The present inventor also succeeded in obtaining a polyester from the transformed plant prepared by the transformation method.

The gene used in the invention is not single and is multiple genes which are linked together to form an operon. The number of kinds of the genes to be linked can appropriately be determined depending upon purposes, but it is preferably 2–100, more preferably 2–50, far more preferably 2–10, most preferably 24. The genes used may be any of known genes and newly cloned genes without being particularly limited to their kinds. Examples of the genes include, in addition to a polyester synthase gene, one or more genes different from the polyester synthase gene (e.g., β-ketothiolase gene, acetoacetyl-CoA reductase gene, etc.). Further examples are described below, but it is not contemplated to limit thereto.

Examples of the polyester synthase gene include the polyester synthase genes (phbC, $phaC_{AC}$, $phbC_{PS}$, $phaC_{PS}$, $phaC2_{PS}$) isolated from *Ralstonia eutropha*, *Aeromonas caviae*, Pseudomonas sp. 61-3 and the like. In the present invention, these genes may be used alone or in the linked form of multiple genes.

The number of kinds of the genes to be linked can appropriately be determined depending upon purposes, but it is preferably 1–100, more preferably 1–50, far more preferably 1–10, most preferably 1–3. The genes used may be any of known genes and newly cloned genes without being particularly limited to their kinds. Examples of the genes include, but are not limited to, β-ketothiolase gene, acetoacetyl-CoA reductase gene, and genes listed below.

(1) Genes involved in reaction pathways (derived from animals, plants, microorganisms, etc.):

Genes encoding enzymes which function in the glycolysis system.

Genes encoding enzymes which function in the glyoxylate cycle.

Genes encoding enzymes which function in the citrate cycle.

Genes encoding enzymes which function in the urea cycle.

Genes encoding enzymes which function in the reductive pentose phosphate cycle.

Genes encoding enzymes which function in the pathway of cholesterol biosynthesis.

Genes encoding enzymes which function in the synthesis of polyketide chains.

Genes encoding enzymes which function in the pathway of fatty acid β oxidation.

Genes involved in the biosynthesis of compounds which have a terpenoid backbone and have 10, 15 or 20 carbon numbers.

(2) Genes derived from particular organisms

Gene or genes involved in the biosynthesis of phosphonomycin, derived from *Streptomyces wedmorensis*.

Gene or genes involved in the biosynthesis of bialaphos, derived from *Streptomyces hygroscopicus*.

Gene or genes involved in the biosynthesis of erythromycin, derived from *Streptomyces erythreus*.

Gene or genes involved in the biosynthesis of penicillin, derived from Penicillium sp, etc.

Gene or genes involved in the biosynthesis of gibberellin and its analogs, derived from *Arabidopsis thaliana*, etc.

Plant gene or genes involved in the biosynthesis of abscisic acid.

(3) Genes classified by reaction substrates

Genes encoding dehydrogenase, oxygenase, reductase, carboxylase, decarboxylase, kinase, phosphatase, deaminase, epimerase, mutase, etc., which enzymes act on compounds with 2–30 carbon numbers as substrates.

Genes encoding protein kinases which phosphorylate proteins having a molecular weight of 3000–300000.

Genes encoding proteases which act on proteins having a molecular weight of 3000–300000 as substrates.

(4) Others

Genes encoding serum albumins from animals.

Genes encoding lactoferrin, lactoglobulin and casein which are present in milk.

Genes encoding α-, β- and γ-subunits of G-protein.

Genes encoding seven-fold transmembrane type receptors such as Substance P receptor.

Gene encoding *Escherichia coli* σ factor.

Gene encoding coat protein from tobacco mosaic virus.

N gene from tobacco.

Tomato cf4 and cf9 genes and their homologues.

Genes encoding MAPK, MAPKK and MAPKKK families from animal and plant.

Genes encoding enzymes belonging to P450 superfamily from animal and plant.

*Arabidopsis thaliana* cpr1-cpr20.

Plant catalase genes catA, catB and catC.

Genes encoding flagellar proteins from microorganisms.

The genes phbA (SEQ ID NO:3), phbB (SEQ ID NO:4) and phbC (SEQ ID NO:2) can be produced by preparing chromosomal DNA from *Ralstonia eutropha* (ATCC 17699), preparing a library, constructing a recombinant vector, introducing the recombinant vector into a host microorganism, subjecting the transformed cells to colony hybridization, and determining a nucleotide sequence. The gene phaC can be obtained from *Aeromonas caviae* strain FA440, and it was introduced into *Alcaligenes eutrophus* and deposited under FERM BP-6038 with National Institute of Bioscience and Human-Technology, Agency of Industrial Science and Technology (1–3, Higashi 1-chome, Tsukuba, Ibaraki, Japan) on Aug. 12, 1996.

Furthermore, the above-described genes can be synthesized chemically or prepared by PCR using each gene as a template.

When making a plant produce a specific substance by using an enzyme as a catalyst, a gene encoding the enzyme and a gene encoding the substrate of the enzyme can be ligated. For example, when poly-3-hydroxybutyrate synthase gene is used as a polyester synthase gene, and β-ketothiolase gene and acetoacetyl-CoA reductase gene are ligated to this, acetyl-CoA is converted into acetoacetyl-CoA by the catalysis of β-ketothiolase, and acetoacetyl-CoA into 3-hydroxybutyryl CoA by the catalysis of acetoacetyl-CoA reductase. Then, poly-3-hydroxybutyric acid can be obtained by the action of poly-3-hydroxybutyrate synthase (FIG. 1).

The promoter used in the present invention is derived from plastid, operon of prokaryote (bacteria), or phage etc., and is anything possible to function as a promoter on plastid chromosome. For example, as the promoter derived from plastid, plastid 16s rRNA promoter, psbD light-responsive promoter, *Arabidopsis thaliana* tRNA-Cys promoter, spinach psaA promoter or corn trnC promoter etc. are listed, and as a promoter derived from bacteria or phage, lac promoter, avrD promoter (*Pseudomonas syringae* pv. Tomato), ORF1-ntrB-ntrC operon promoter (*Rhizobium leguminosarum*) or phage T7 gene 10 promoter are listed. The number of promoters is preferably 1 or 2.

In order to ligate multiple genes of interest, in addition to the method for directly litigating them using ligase, there can be used the method which comprises chemically synthesizing an appropriate linker whose length is 4 to 100 nucleotides and ligating the genes using the said linker as a bridge. Alternatively, there can be also used another method which comprises ligating each gene to each distinct vector, preparing fragments containing the said genes by restriction enzyme treatment and ligating each fragment using ligase. In this method, it is preferable that using the gene of interest as a template, primers specific for the gene (15 to 50 nucleotides in length) are prepared to amplify the fragment by polymerase chain reaction (PCR). As a DNA polymerase used for the amplification, LA Taq DNA polymerase (Takara), AmpliTaq (Perkin Elmer), Pfu DNA polymerase (Stratagene) and the like can be used, but it is not limited to them. The DNA is amplified for 10 to 40 cycles using the following steps as a cycle: 5 seconds to 3 minutes at 80° C. to 100° C., preferably 5 seconds to 2 minutes at 94° C. for denaturation, 5 seconds to 5 minutes at 40° C. to 72° C., preferably 5 seconds to 2 minutes at 50° C. for annealing, and 30 seconds to 10 minutes at 65° C. to 75° C., preferably 30 seconds to 3 minutes at 72° C. for elongation. In order to sufficiently denature the template DNA and primers, the denaturation may be carried out for 1–3 minutes at 80° C. to 100° C. (preferably 94° C. to 95° C.) before the said amplification cycle, or to elongate completely the amplified DNA, the elongation may be carried out for 2–10 minutes at 72° C. after the said amplification cycle.

By ligating a promoter to the site upstream of the genes obtained according to the above process, an operon wherein multiple genes are controlled by one or several promoters is formed. The method of ligating the promoter is not particularly limited, but any method can be used, e.g. the treatment of restriction enzyme site by ligase.

The operon formed as above is ligated to a vector for introducing it into the plastid of a plant. As a vector used in the present invention, plasmid vector, cosmid vector, phage vector and the like can be used, but among them, plasmid vector is preferable. As the plasmid vector, pUC plasmid such as pUC18 (Takara Shuzo) or pUC119 (Takara Shuzo), pBI plasmid such as pBI121 or pBI101, pBluescript SK+ (Stratagene), pGEM-T (Promega), pGEM-3, pGEM-4, pCR2.1(Invitrogen) and the like can be used. On the other hand, as the cosmid vector, pJB8, c2RB, pcos1EMBL and the like can be used, and as the phage vector (e.g. λ phage), Charon4A, Charon21A, Charon32, EMBL3, EMBL4, λgt10, λgt11, λZAP and the like can be used. However the vector is not limited to the examples above listed.

Multiple genes to be expressed should be inserted into a vector so that each gene can fully exhibit its function. Hence, not only the promoter and gene of interest but also a terminator, operator, attenuator, drug-resistant gene or the like can be introduced into the said operon. In this case, 3'-regulatory region of plastid psbA gene as a terminator, lactose operator of *Escherichia coli* etc. as an operator, tryptophan synthesis operon attenuator of *Escherichia coli* etc. as an attenuator, and spectinomycin-resistant gene, streptomycin-resistant gene, kanamycin-resistant gene, hygromycin- resistant gene, bialaphos-resistant gene, blasticidin S resistant gene or the like can be used as a drug-resistant gene.

The plant to be transformed in the present invention refers to any of an entire plant body, plant organs (e.g. leaf, petal, stem, root, seed, etc.) , plant tissues (e.g. epidermis, phloem, parenchyma, xylem, vascular bundle, palisade layer or spongy parenchyma) or plant culture cell. As the plant used for transformation, for example, the plants belonging to Solanaceae, Gramineae, Brassicaceae, Compositae, Pedaliaceae, Oleaceae, Myrtaceae, Rosaceae, Leguminosae, Palmae or Rubiaceae can be adopted. Examples of the plants belonging to these families include, but are not limited to plants listed below.

Solanaceae: Tobacco (*Nicotiana tabacum*), Potato (*Solanum tuberosum*)

Gramineae: Corn (*Zea mays*), Rice (*Oryza sativa*)

Malvaceae: Cotton (*Gossypium hirsutum*), Okra (*Abelmoscus esculentum*)

Brassicaceae: Thale-cress (*Arabidopsis thaliana*), Rape (*Brassica napus*)

Compositae: Sunflower (*Helianthus annuus*), Chrysanthemum (*Crysanthimum indicum*)
Pedaliaceae: Sesame (*Sesame indica*), Castor-oil plant (*Ricinus communis*)
Oleaceae: Olive (*Olea europaea*)
Myrtaceae: Bastard box (*Eucalyptus globulus*), Guava (*Psidium guava*)
Rosaceae: Rose (*Rosa sinnis*)
Theaceae: Camellia (*Camellia japonica*)
Leguminosae: Milk vetch (*Astragalus sinicus*), Soybean (*Glycine max*)
Palmae: Coconut (*Cocos nucifera*)
Sterculiaceae: Cacao (*Theobroma cacao*)
Rubiaceae: Coffee tree (*Coffea arabica*)

The above-stated recombinant vectors can be introduced into the plastid of a plant by the ordinary transformation methods including, for example, particle gun, PEG method, electroporation and the like. For instance, when the particle gun is used, the plant body, plant organs and plant tissues themselves may be used directly, may be used after preparing their segments, or it may be also possible to prepare the protoplast beforehand and use it. Thus, the prepared sample can be treated by a gene-transfer instrument (e.g. Biolistic PSD-1000/He (BIO-RAD)). The conditions of the treatment depend on plants or samples, but generally it is carried out under the pressure of approx. 100 to 2,000 psi and the distance of 0.5 to 20 cm.

When a plant culture cell is used as a host, a recombinant vector is introduced into the culture cell by the transformation method such as particle gun or electroporation.

The tumor tissues, chutes, capillary roots or the like obtained after the transformation can be directly used for cell, tissue or organ culture, and they can also be redifferentiated to the plant body by administering plant hormones (auxin, cytokinin, gibberellin, abscisin acid, ethylene, brassinolide, etc.) according to the method for plant tissue culture which is conventionally known. In the transformed plant cell, the introduced gene is inserted into the plastid chromosome gene by homologous recombination.

The confirmation that the gene was integrated into the plant or not can be carried out by PCR, Southern hybridization, Northern hybridization and the like. Taking PCR as an example, the process is carried out by preparing DNA from the transformed plant and designing primers specific for the DNA. Here, PCR can be carried out under the same conditions as the ones used for the preparation of the said plasmid. Then, the amplified product is subjected to agarose gel electrophoresis, polyacrylamide gel electrophoresis or capillary zone electrophoresis, is stained with ethidium bromide, SYBR Green solution, etc., and finally can be confirmed to be transformed by detecting the amplified product as a band. Furthermore, it is also possible to detect the amplified product by carrying out PCR wherein the primer previously labeled by e.g. fluorescent dye is used. In addition, there is also the method which comprises attaching the amplified product to a solid phase such as microplate and confirming the existence of the product by the fluorescent or enzyme reaction.

In determining whether the polyester synthase gene integrated into the plastid is expressed or not, the appropriate method for detecting a polyester obtained by the expression of the said gene can be used. For example, the polyester synthesis can be confirmed by mass spectrometry, gas chromatography or the like.

Since in this invention a foreign gene is introduced into a plant cell by homologous recombination using a gene of the plastid chromosome, it is possible to control exactly the position at which the gene for transformation is inserted by ligating the gene of the plastid chromosome to a vector. Taking plastid as an example, a gene called rbcL and another gene called ORF512 are adjacent to each other in the chromosome. Now ligating these two genes to a vector and inserting an operon used for the present invention between rbcL and ORF512, by the homologous recombination after transformation, the said operon comes to be inserted at the position in the plastid chromosome, where originally rbcL and ORF512 exist. On the other hand, inserting the operon somewhere in the sequence of rbcL or ORF512 gene, the rbcL or ORF512 gene is discontinued by the operon and accordingly the function of the said gene is lost.

Thus, according to the method of selecting the gene which exists in the plastid, the position where the operon is inserted can be set optionally, and also the operon can be inserted in such a manner as to or not as to damage the original function of the plastid. Furthermore, when multiple genes not derived from microorganisms but from animals or plants are introduced, it is possible to express easily without following the conventional way wherein promoters are ligated to every distinct gene.

Since plastid has the feature of maternal inheritance, it is advantageously possible to prevent the introduced genes from diffusing in the environment via pollens and so on. That is to say, when a plant is pollinated with the pollens of a wild strain, foreign genes are inherited in the seeds, but on the contrary, when a wild strain is pollinated with the pollens of a transformed plant, foreign genes are not inherited in the seeds. This feature of the present invention is extremely advantageous to alleviate the influence on the environment at the occasion of producing various transformed plants from now on, and to create the hybrid progeny.

By culturing or cultivating the transformants obtained as above-stated, polyester can be produced.

When the transformants are plant cells or plant tissues, the culture can be carried out by using an ordinary culture medium for plants, for example, MS basal medium (Murashige, T. & Skoog, F. (1962) Physiol. Plant. 15: 473). LS basal medium (Linsmaier, E. M. & Skoog, F. (1965) Physiol. Plant.18: 100) or protoplast culture medium (a medium modified from LS medium). As the culture method, an ordinary solid culture can be adopted, but a liquid culture can be preferably adopted.

0.5–40 g fresh weight/l of plant cells, tissues or organs are inoculated into one of the above-listed medium, and cultured, adding as necessary NAA, 2.4-D, BA or kinetin etc. The pH of the medium at the beginning of culture is adjusted to 5.6–5.8, the culture temperature is generally 25–30° C., preferably around 25° C., and the culture is carried out for 1–8 weeks stirring at 20–120 rpm.

When the transformant is a plant body, it can be cultivated or water-cultured in the field or in a green house.

At the end of the culture, the general method for purifying polyesters can be used to collect the polyester from the culture. Then, depending on the state of the cultured cells or cultured tissues, or the plant organs or plant body, they may be washed with 50% ethanol or methanol, followed by purification of the polyester.

When the polyester is collected from cultured cells or tissues, the cells or tissues are destroyed by cytolysis process using enzymes such as cellulase or pectinase, ultrasonication or grinding process, followed by removing an insoluble by e.g. filtration or centrifugation to yield a crude polyester solution.

In order to further purify the polyester from the above-stated crude polyester solution, not only the solvent extraction method using chloroform or ethyl acetate as a solvent, but the ordinary purification methods can be also used. For example, gas chromatography, liquid chromatography, mass spectrometry, NMR and so on can be used alone or in combination as appropriate.

When the polyester is collected from the plant organs or plant body, the above-stated crude polyester solution is prepared by e.g. ultrasonication or grinding process, the polyester is extracted from the solution by using chloroform, and then following the same purification method as stated above, the polyester can be obtained.

So obtained polyester is the copolymer of 3-hydroxyalkanoic acid (the degree of polymerization: 1 to 1,000,000), represented by the following formula I:

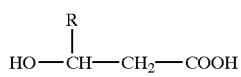

(I)

wherein R is a hydrogen atom or a $C_{1-4}$ alkyl group.

For example, the said copolymer is poly-3-hydroxybutyric acid represented by the following formula II:

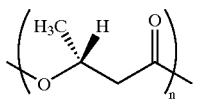

(II)

wherein n is an integer from 1 to 1,000,000; or the said copolymer has the structure of polyhydroxyalkanoic acid represented by the following formula III:

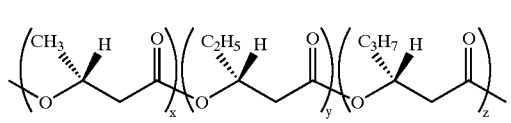

(III)

wherein
x is an integer from 0 to 1,000,000;
y is an integer from 0 to 1,000,000;
z is an integer from 0 to 1,000,000; but
where x, y and z should not be 0 at the same time.

In order to check that a polyester synthase was generated or not, mass spectrometry, gas chromatography, or the like can be used.

When the polyester synthase gene is introduced into a nucleus chromosome, the expressed protein is localized to a plastid by a previously added transit peptide. In this case, it is very rare that three types of proteins which are necessary for producing a polyester transfer effectively to one among several tens of plastids in a cell. For this reason, the ratio of these three types of proteins is different in each plastid, and some proteins may be lost while transferring to the plastids.

In contract to this, when the gene for the polyester synthase is introduced into a plastid chromosome, since the gene in an operon which was introduced into the plastid is controlled by a promoter, three types of proteins are expressed in a plastid and the ratio of expression is always 1:1:1, and this is the same ratio as when these are expressed in a microorganism. That is, the production efficiency of polyester to the expression of proteins is extremely high.

EXAMPLES

The following examples illustrate the present invention more specifically. However, it is contemplated that the technical scope of the present invention is not limited to these examples.

Example 1

Preparation of an Operon Containing a Polyester Synthase Gene, and Transformation In this example, we introduced an operon containing a polyester synthase gene derived from bacteria into a plastid by homologous recombination, and tried to create a plant which produces a polyester in its plastid. That is to say, using an phb operon which encodes each of three enzymes producing poly-3-hydroxybutyric acid ester (poly-3-hydroxybutyrate synthase (phbC), β-ketothiolase (phbA) and acetoacetyl-CoA reductase (phbB)), we introduced the genes of a microorganism into the plastid by plastid transformation, and we examined from the result of the expression whether the plant can acquire a metabolic system derived from the microorganism as a new character.

The following conditions were provided: tobacco as an examined plant, spectinomycin-resistant gene (aminoglycoside-3-adenyltransferase (aadA) gene) as a drug-selective marker of transformation, plastid 16S rRNA promoter (Prrn; SEQ ID NO: 16) as a promoter controlling an operon, and plastid psbA 3'-regulatory region (SEQ ID NO: 17) as a terminator. In order to make sure that the homologous recombination is carried out in the plastid chromosome, the genes rbcL and ORF512 which exist in the plastid were used (rbcL-ORF512; SEQ ID NO: 18). In passing, aadA gene is available from ATCC, as the following numbers:

1: ATCC Number: 67113 Designations: pMON30 [SR20] Organis
2: ATCC Number: 77185 Designations: pAM34 Sites: PolyI
3: ATCC Number: 77186 Designations: pAM35 Sites: PolyI
4: ATCC Number: 87150 Designations: pBSL175 Sites: Pol
5: ATCC Number: 87119 Designations: pIC552 Sites: Poly
6: ATCC Number: 87626 Designations: pHP45omegavph Sites Moreover, in the sequence as shown in SEQ ID NO: 18, rbcL represents the region from the $227^{th}$ to the $1660^{th}$ and ORF512 represents the region from the $2425^{th}$ to the $3963^{rd}$.

Figure 3:
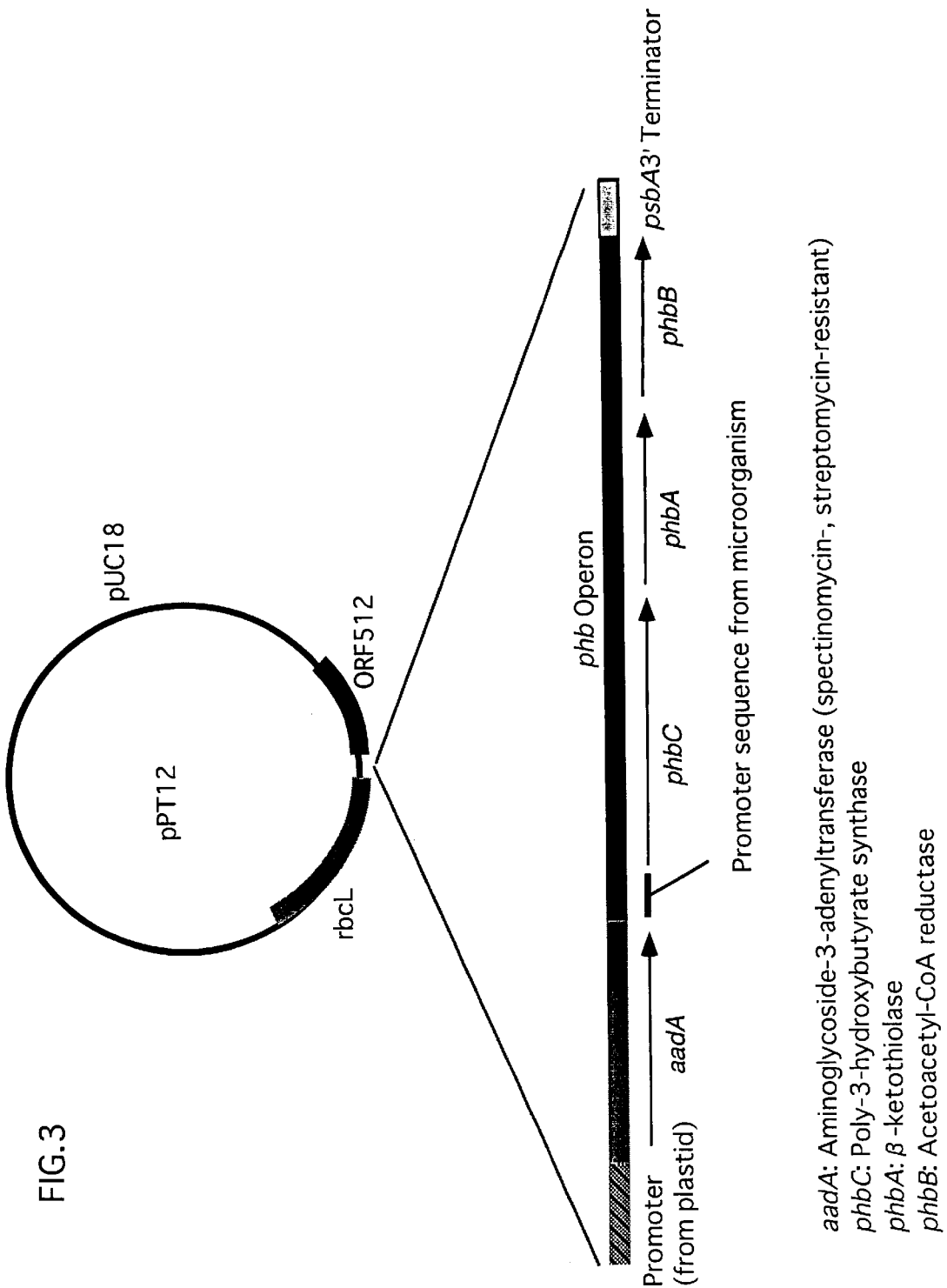
FIG. 3 shows the construction of plasmid pPT12.

The promoter and aadA were ligated to the site upstream of phb operon to prepare plasmid pPT12 (FIG. 3).

Figure 4:
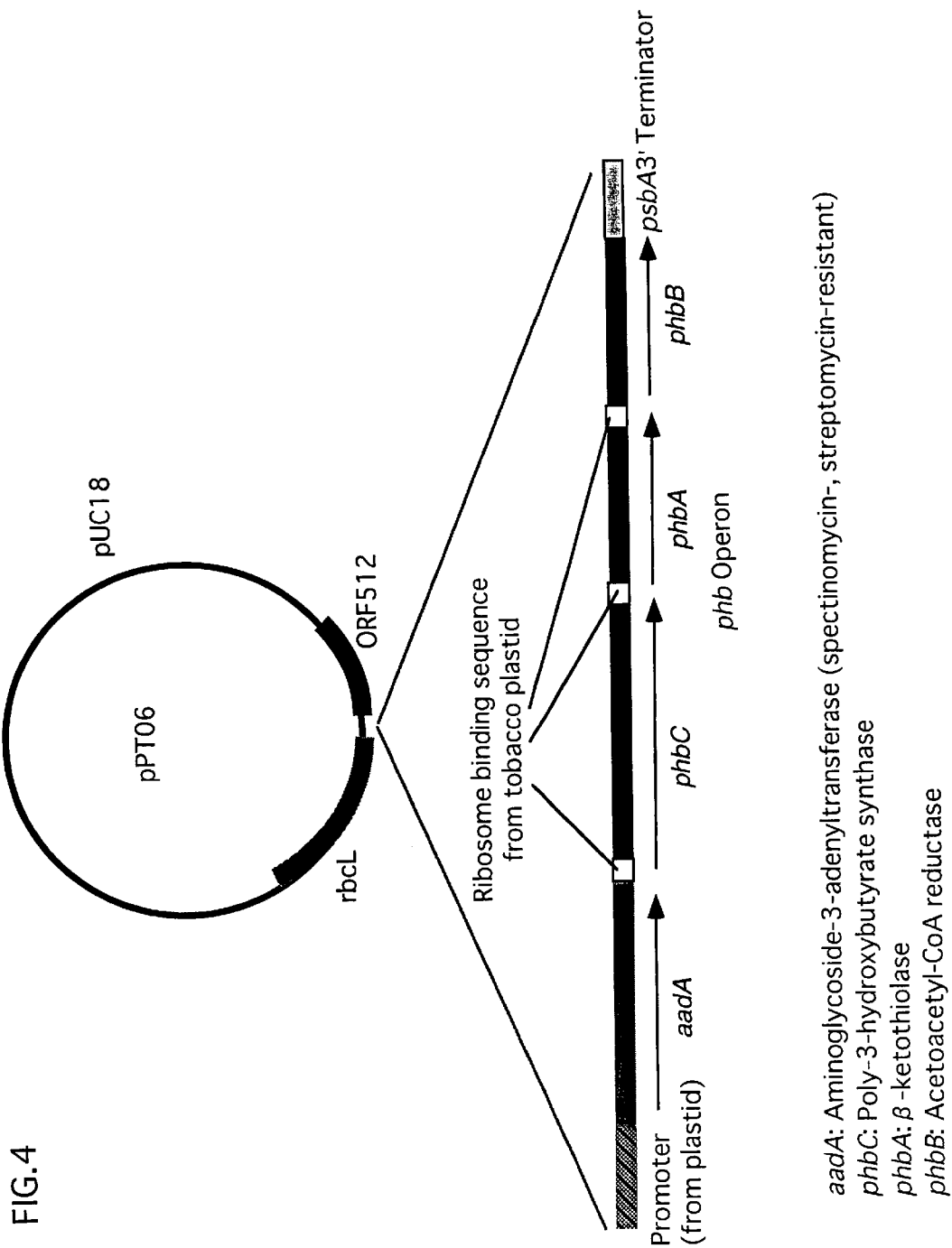
FIG. 4 shows the construction of plasmid pPT06.

Since it is not clear whether the ribosome binding site, which is needed to translate a transcribed mRNA into a protein, acts in plastid, an operon in which the sequence of the ribosome binding site of plastid gene rbcL (AGGGAGGGA) was added to the site upstream from the translational initiation site of each phb operon gene (phbC, phbA and phbB) was prepared. Then, this operon was ligated to aminoglycoside-3-adenyltransferase (aadA) in the forward direction to form a new operon, thereby preparing the plasmid pPT06 used for transformation (FIG. 4).

The methods for preparing each plasmid are illustrated below.

1. Preparation of Plasmid (1) Preparation of pPL1

The gene encoding aminoglycoside-3-adenyltransferase (aadA) (SEQ ID NO: 5) was amplified by PCR using the primer SPEC-U and SPEC-L.

SPEC-U: TCTGGATCCATGGCTAGTGAA
    GCGGTTATC    (SEQ ID NO: 6)

SPEC-L: TTGAGATCTAGACTGCAGTTATTTGC-
    CGACTACCTTGG    (SEQ ID NO: 7)

The conditions of PCR were as follows:
Composition of reaction solution:

| 10 × PCR buffer | 5 µl |
| dNTP mix (10 mM each) | 0.5 µl |
| Primer SPEC-U (10 pmol/µl) | 1 µl |
| Primer SPEC-L (10 pmol/µl) | 1 µl |
| Template DNA | 0.5 µl |
| Taq polymerase | 0.5 µl |
| Water | 41.5 µl |
| Total amount | 50 µl |

Reaction Cycle

After carrying out a reaction at 94° C. for 1 minute, a cycle of 30 seconds at 94° C. for denaturation, 30 seconds at 50° C. for annealing and 5 minutes at 72° C. for elongation were repeated for 30 cycles. After 30 cycles, a reaction at 72° C. for 5 minutes was carried out.

Then, after PCR, the amplified product was cloned into pUC18 to obtain the plasmid pPL1 containing aadA gene.

(2) Preparation of pPL2

The gene phbC has been cloned from *Ralstonia eutropha* (ATCC 17699).

First, *Ralstonia eutropha* (ATCC 17699) was cultured in 100 ml of LB medium (1% yeast extract, 0.5% tryptone, 0.5% sodium chloride, 0.1% glucose and pH7.5) at 30° C. overnight, and chromosome DNA was obtained by hexadecyl trimethylammonium bromide method (Currnt Protocol in Molecular Biology, Vol. 1, P2.4.3., 1994, John Wiley & Sons).

Second, in order to obtain a DNA fragment containing *Ralstonia eutropha* phbC, phbA and phbCB, the chemical synthesis of oligonucleotide (Primers phb-U and phb-L) was carried out.

phb-U: ATGGATCCCGGGCAAGTACCTT
    GCCGACAT    (SEQ ID NO: 8)

phb-L: TCCGGATCCTATGCCCAACAAGG
    CACTAAGA    (SEQ ID NO: 9)

With these primers, the partial phbC gene was amplified by PCR wherein the chromosome DNA of *Ralstonia eutropha* was used as a template. In this PCR, a cycle of reactions of 1 minute at 94° C. for denaturation, 2 minutes at 63° C. for annealing and 4 minutes at 72° C. for elongation was repeated for 30 cycles. The obtained PCR product which comprises the phb operon gene containing phbC, phbA and phbCB (SEQ ID NO: 1; 4984 bp) was cloned into pUC18.

In the phb operon (SEQ ID NO: 1), phbC had the sequence from the $842^{nd}$ to the $2611^{st}$, phbA had the sequence from the $2696^{th}$ to $3877^{th}$, and phbB had the sequence from the $3952^{nd}$ to the $4692^{nd}$. From the phb operon gene containing phbC, phbA and phbCB obtained by the above-stated method, phbC was amplified by PCR using rbs-CU and rbs-CL.

rbs-CU: ATCGGATCCAGGGAGGGAATCATGGC-
    GACCGGCAAAGGCGCG    (SEQ ID NO: 10)

rbs-CL: AGCAAGCTTTTCAATGGAAACGGG
    AGGGAACCTG    (SEQ ID NO: 11)

The conditions of PCR were as follows. The composition of the reaction solution was the same as described in (1) except primers.

Reaction Cycle 1. 95° C. 1 minutes
2. (94° C. 1 minute, 63° C. 2 minutes, 72° C. 4 minutes)× 30 cycles
3. 72° C. 5 minutes Then, the amplified product so-obtained was cloned into pUC18 to obtain the plasmid pPL2 containing phbC gene (SEQ ID NO: 2).

(3) Preparation of pPL3

From the phbB operon obtained by the method described in (2), DNA encoding phbA was prepared by PCR using the following primers.

rbs-AU: ATCAAGCTTAGGGAGGGAACAATGACT-
    GACGTTGTCATCG    (SEQ ID NO: 12)

rbs-AL: AGAGAATTCCCTTGATTGGCTTCG
    TTATCGTCGC    (SEQ ID NO: 13)

The conditions of PCR were as follows. The composition of the reaction solution was the same as described in (1) except primers.

Reaction Cycle 1. 94° C. 1 minutes
2. (94° C. 30 seconds, 50° C. 30 seconds, 72° C. 2 minutes)×30 cycles
3. 72° C. 5 minutes As a result, the nucleotide sequence of 1.2 kbp of phbA gene was determined (SEQ ID NO: 3). The obtained amplified product was cloned into pUC18 to obtain the plasmid pPL3 containing phbA gene.

(4) Preparation of pPL4

0.8 kb of phbB gene (SEQ ID NO: 4) was obtained by the same method as the one by which phbA gene was prepared, using the following primers.

rbs-BU: ATCGAATTCAGGGAGGGAACATGACT-
    CAGCGCATTGCGTATGTG    (SEQ ID NO: 14)

rbs-BL: AGAGGATCCCAGGCCGGCAGGT
    CAGCCCATATGC    (SEQ ID NO: 15)

The composition of reaction solution is the same as described in (1) except primers.

Reaction cycle is the same as described in (3).

The obtained amplified product was cloned into EcoR-BamHI sites of pUC18 to obtain the plasmid pPL4 containing phbB gene (SEQ ID NO: 4).

(5) Preparation of pPL5

BamHI-BglII fragment containing aadA of pPL1 was inserted at BamHI site upstream of phbC in pPL2 to prepare the plasmid pPL5 wherein aadA and phbC were aligned in the forward direction.

(6) Preparation of pPL6

After ligating a HindIII-EcoRI fragment containing phbA of pPL3 to an EcoRI-KpnI fragment containing phbB of pPL4, the ligated fragment was inserted into HindIII-KpnI sites of pUC18 to prepare the plasmid pPL6 wherein phbA and phbB were aligned in the forward direction.

(7) Preparation of pPL7

After ligating a BamHI-HindIII fragment of pPL5 to a HindIII-KpnI fragment of pPL6, the ligated fragment was inserted into BamHI-Kpn1 sites of pUC18 to prepare the plasmid pPL7 wherein aadA, phbC, phbA and phbB in this order were aligned in the forward direction.

(8) Preparation of pPL8

Using primers phb-U and phb-L (See (2)), phb operon was amplified with DNA which was prepared from *Ralstonia eutropha* as a template. The conditions of PCR were the same as described in (2).

First, the amplified fragment was cloned into BamHI site of pUC18 to obtain the plasmid pCAB3 containing the operon wherein rbs was not ligated at the upstream of each of phbC, phbA and phbB.

Second, BamHI-BamHI fragment containing phb operon of pCAB3 was inserted into BglII site of pPL1 in the order of aadA, phbC, phbA and phbB to prepare pPL8.

(9) Preparation of pPT 5

(9-1) Preparation of pCT11

Figure 2:
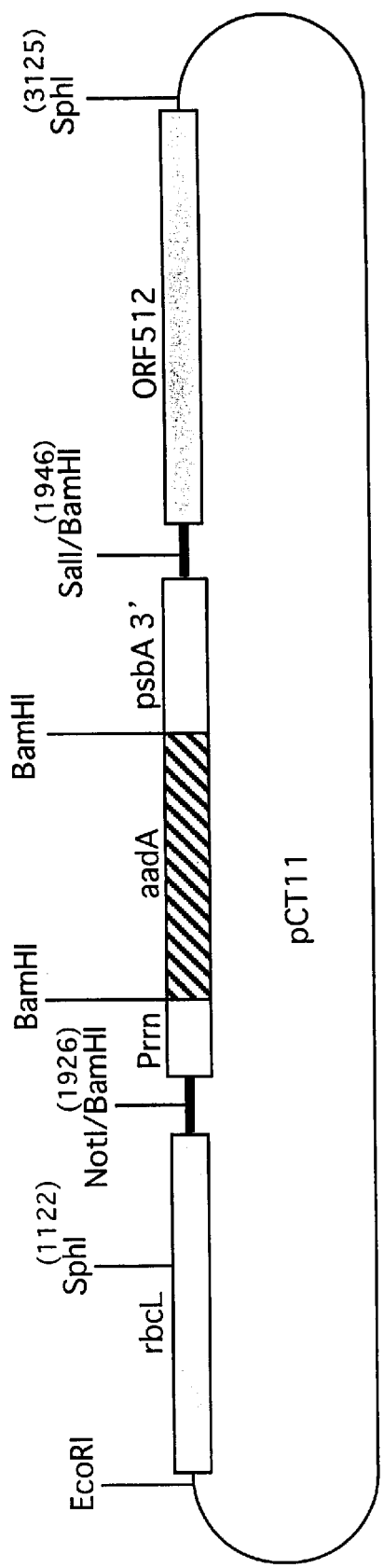
FIG. 2 shows the construction of plasmid pCT11.

On pUC18, tobacco plastid 16S rRNA promoter sequence (approx. 0.12 kb) (Prrn) was added to the upstream site of aadA, and tobacco plastid psbA 3'-regulatory region (terminator) (approx. 0.4 kb) was added to its downstream site. Since NotI and SalI recognition sites were respectively added to 5'-terminus of the promoter sequence and 3'-terminus of the terminator, the plasmid was treated with NotI and SalI. After the resulting NotI-SalI fragment was blunt-ended, two BamHI sites (the $1926^{th}$ and $1946^{th}$ positions of the nucleotide sequence as shown in SEQ ID NO: 18) between rbcL and ORF512 were also given the same treatment. Then, the said NotI-SalI fragment was inserted between two sites, and the genes aligned in the order of rbcL, Prrn, aadA, psbA 3' and ORF512 were assembled onto pUC19 (between EcoRI and SalI) to obtain pCT11 (Svab, Z. and Maliga, P. (1993) Proc. Natl. Acad. Sci. USA 90: 913–917. Shikanai, T. et al. (1998) Proc. Natl. Acad. Sci. USA 95: 9705–9709) (FIG. 2).

The rbcL-ORF512 gene fragment used in this process is the one having nucleotide Nos. 57361–61620 in tobacco plastid chromosome (Gene Bank accession #Z00044).

(9-2) Preparation of pPT05

A fragment of pCT11 which was cut out between the SphI site in rbcL (1122) and the SphI site of the vector on 3' side of ORF512 was inserted into SphI site of pUC18 to prepare pPT01.

After removing aadA by giving enzyme treatment to BamHI sites which exists on the both sides of aadA of pPT01, pPT05 having genes aligned in the order of rbcL, Prrn, psbA3' and ORF512 was prepared by ring-closure caused by self-litigation.

(10) Preparation of pPT06 and pPT12

BamHI-BamHI fragment of pPL7 was inserted into BamHI site of pPT05 so that aadA comes at the back of Prrn to prepare pPT06 (FIG. 4).

BamHI-BamHI fragment of pPL8 was inserted into BamHI site of pPT05 so that aadA comes at the back of Prrn to prepare pPT12 (FIG. 3).

2. Transformation

A particle gun was used to carry out the transformation in this example. Regarding the tobacco used as a host, the seed was cultured on MS medium aseptically and grown to the plant body, and the leaf or segment of which diameter was approximately 2 to 7 cm was used. The microparticles such as gold or tungsten were coated with the plasmid DNA. The said leaf or segment was placed right side down (but right side up is also possible) on RMOP medium (Svab, Z. et al., Proc. Natl. Acad. Sci. USA (1990)87: 8526), and the said particles were shot therein (1350 psi, distance: 5–15 cm). Then, the said leaf or segment was cultured on RMOP medium for two days in the light (approx. 3000 lux) at 25° C. After two days, this leaf was cut to approximately 5–10 mm of small pieces, and they were cultured on RMOP medium containing spectinomycin (500 μg/ml) for two days in the light (approx. 3000 lux) at 25° C. After continuing the culture for 3–6 weeks, the generated callus or redifferentiated plant was subcultured on MS medium containing spectinomycin (500 μg/ml) for further 2–3 weeks. Then, the said calllus or redifferentiated plant was subcultured on MS medium containing spectinomycin (500 μg/ml) to stimulated its rooting.

So obtained redifferentiated individuals had both transformed plastid and non-transformed plastid. Thus, the leaf of this redifferentiated individuals was cut to pieces, which were placed on RMOP medium containing spectinomycin (500 μg/ml), and the redifferentiation was carried out once again. The redifferentiated individuals were radicated on MS medium (Murashige, T. & Skoog, F. (1962) Physiol. Plant. 15: 473) containing spectinomycin (500 μg/ml). Then, they were transferred to plant pots with the earth, were acclimatized, and cultivation was carried out to obtain the redifferentiated individuals (transformed plants; epigeal stem 45–80 cm).

Example 2

Confirmation of Introduced Gene (1) Confirmation by PCR

The existence of spectinomycin-resistant gene and three polyester synthase genes in the redifferentiated individuals was confirmed by PCR.

Each template DNA was extracted from each leaf of the redifferentiated individuals (6 individuals) by CATB method. The primers specific for each gene were the same as the ones which were used for constructing plasmid.

Figure 5:
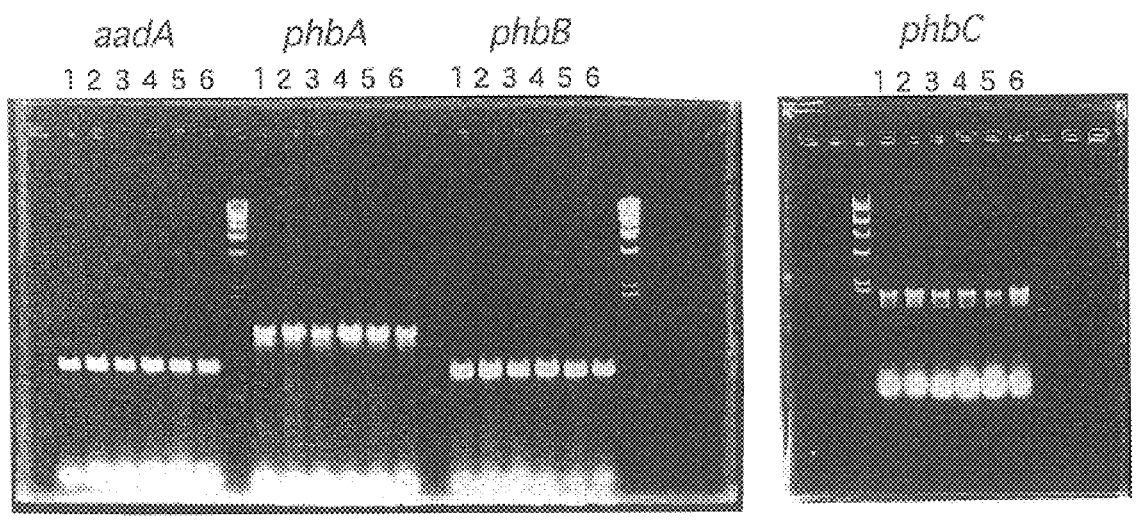
FIG. 5 is a photograph showing the results of agarose gel electrophoresis.

The conditions of PCR for each gene were the same as described in Example 1. After PCR, electrophoresis on agarose gel was carried out for the reaction product, and the existence of each gene was confirmed by staining with ethidium bromide. As a result, regarding 4 types of genes introduced into all six individuals, each band was confirmed (FIG. 5). Because these genes were obtained from the individuals which were expressed under the control of promoter specific for plastid and were selected by spectinomycin, it was shown that the transformants had the activity of spectinomycin-resistant gene and the said 4 types of genes were introduced into the plastid.

(2) Confirmation of polyester productivity by gas chromatography-mass spectrometry (GC-MS)

In order to determine whether an operon introduced into the redifferentiated individual has been expressed, the productivity of the polyester (poly-3-hydroxybutyric acid ester) caused by the expression product of 3 polyester synthase genes was analyzed.

After freeze-drying and crushing the leaf of the redifferentiated individual, it was subjected to chloroform extraction using Soxhlet extractor. After washing the extract with 1M NaCl solution twice followed by concentration, 10–15 volumes of methanol were added. The precipitate was collected by filter and dissolved in chloroform. Using the concentrated solution as a sample, it was subjected to ethanolysis under acidic conditions (sample 0.1 ml, ethanol 0.34 ml, hydrochloric acid 0.04 ml, 100° C., 4 hours). After the reaction solution was washed with 1.2 ml of 1M NaCl solution, chloroform fraction was collected. After the chloroform fraction was dehydrated on sodium sulfate, it was analyzed by gas chromatography-mass spectrometry (GC-MS).

Conditions of GC-MS: capillary column HP5 (25 m), 45° C.→250° C. (5° C./min)

Figure 6A:
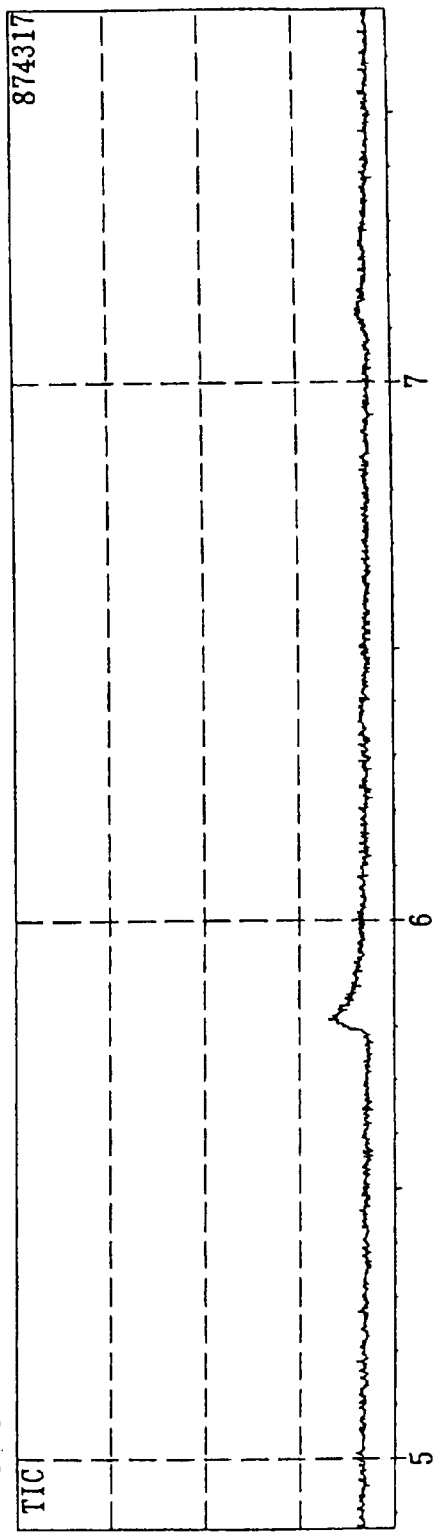
FIGS. 6A and 6B show the results obtained by gas chromatography and mass spectrometry.
Figure 6B:
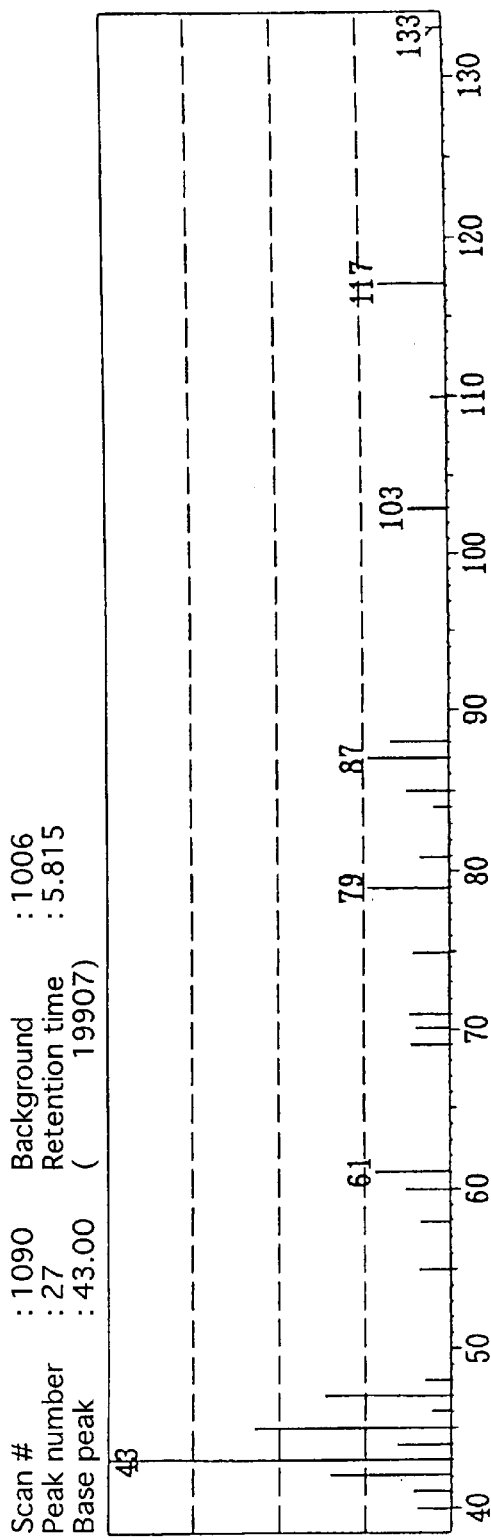

As a result, the peaks of 3-hydroxybutyric acid ethylester derived from PHB was detected in the transformant (see the peak of 5.8 min. in FIG. 6A with regard to GC, and see the peaks of 117, 103, 87, 71, 60 and 43 in FIG. 6B with regard to MS). However, such peaks were not detected in the non-transformant. Therefore, it was found that the polyester-biosynthesizing operon derived from microorganism was integrated into the plastid of the plant and functioned normally.

(3) Confirmation of polyester productivity by fluorescent microscopy

The leaves of the redifferentiated individual of tobacco with 4 types of genes introduced were cut into approx. 0.5 cm squares, decompressed while soaking them in the fixative (2.5% glutaraldehyde, 100 mM sodium phosphate buffer, pH 7.4), and left stationarily for 2–4 hours to infiltrate the fixative therein. This sample was cut by razor to make thin sections, stained with Nile blue A, and observed with fluorescent microscopy.

Given an excitation with 460 nm, the entire chloroplast turned red, and among others, the chloroplast containing polyester turned strong red. Next, given an excitation with 546 nm, the entire tissues remained green, and the chloroplast containing polyester turned to orangish yellow.

From these results, it was found that the polyester was effectively produced in the chloroplast and it was confirmed that the introduced polyester-biosynthesizing operon functioned well.

This specification includes part or all of the contents as disclosed in the specification and/or drawings of Japanese Patent Application No. 11-225832 and No. 11-225839, which are priority documents of the present invention.

ADVANTAGEOUS EFFECT OF THE INVENTION

According to the present invention, there are provided the method for transforming plants, transformed plants, and process for preparing polyester. By the method of the present invention, when multiple genes derived from nucleus chromosomes of animals or plants are introduced, they can be expressed easily without ligating promoters to each gene, and for example, polyesters can be obtained in high yields.

What is claimed is:

1. A method for the transformation of a plant wherein the method comprises:
   (a) preparing a vector and an operon wherein the operon comprises, in a 5'-3' orientation, a promoter, a plurality of 2 to 10 genes of interest and, with each gene of the plurality, a ribosome binding site of a plastid gene, said site being located at a position upstream of each of said genes;
   (b) ligating the operon to the vector;
   (c) integrating the resulting recombinant vector into a plastid chromosome; and
   (d) obtaining the resulting transformed plant which has the plastid chromosome comprising the operon.

2. The method of claim 1 wherein said genes of interest are a polyester synthase gene and a gene different from the polyester synthase gene.

3. The method of claim 1 wherein said genes of interest are a polyester synthase gene, a β-ketothiolase gene, and an acetoacetyl-CoA reductase gene.

4. The method of claim 3 wherein said polyester synthase gene is a poly-3-hydroxybutyrate synthase gene.

5. The method of claim 1 wherein said plant belongs to any family selected from the group consisting of Solanaceae, Gramineae, Malvaceae, Brassicaceae, Compositae, Pedaliaceae, Oleaceae, Myrtaceae, Rosaceae, Theaceae, Leguminosae, Palmae, Sterculiaceae, and Rubiaceae.

6. The method of claim 5 wherein said plant belongs to the species *Nicotiana tabacum*.

7. A transformed plant in which the operon that comprises, in a 5'-3' orientation, a promoter, a plurality of from 2 to 10 genes of interest and, with each gene of the plurality, a ribosome binding site of a plastid gene, located at a position upstream of said gene, wherein said operon is integrated into a plastid chromosome.

8. The transformed plant of claim 7 wherein said genes of interest are a polyester synthase gene and a gene different from the polyester synthase gene.

9. The transformed plant of claim 7 wherein said genes of interest are a polyester synthase gene, a β-ketothiolase gene, and an acetoacetyl-CoA reductase gene.

10. The transformed plant of claim 9 wherein said polyester synthase gene is a poly-3-hydroxybutyrate synthase gene.

11. The transformed plant of claim 7 wherein said plant belongs to any family selected from the group consisting of Solanaceae, Gramineae, Malvaceae, Brassicaceae, Compositae, Pedaliaceae, Oleaceae, Myrtaceae, Rosaceae, Theaceae, Leguminosae, Palmae, Sterculiaceae, and Rubiaceae.

12. The transformed plant of claim 11 wherein said plant belongs to the species *Nicotiana tabacum*.

13. A process for preparing a polyester comprising:
    (a) integrating a recombinant vector to which is ligated an operon comprising, in a 5'-3' orientation, a promoter, a polyester synthase gene, a plurality of from 1 to 10 genes different from the polyester gene and, with the polyester synthase gene and seach gene of the plurality, a ribosome binding site of a plastid gene located at a position upstream of said gene, into the plastid chromosome of a plant to transform the plant;
    (b) culturing or cultivating the obtained transformed plant; and
    (c) collecting the polyester from the cultured or cultivated plant.

14. The process of claim 13 wherein said polyester synthase is a poly-3-hydroxybutyrate synthase gene.

15. The process of claim 13 wherein said operon comprises, in addition to said polyester sylnthase gene, a β-ketothiolase gene and an acetoacetyl-CoA reductase gene.

16. The process of claim 13 wherein said plant belongs to any family selected from the group consisting of Solanaceae, Gramineae, Malvaceae, Brassicaceae, Compositae, Pedaliaceae, Oleaceae, Myrtaceae, Rosaceae, Theaceae, Leguminosae, Palmae, Sterculiaceae, and Rubiaceae.

17. The process of claim 16 wherein said plant belongs to the species *Nicotiana tabacum*.

18. The process of claim 13 wherein said polyester is a polymer comprising 3-hydroxyalkanoic acid represented by following formula I:

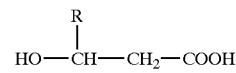

wherein R represents a hydrogen atom or a $C_{1-4}$ alkyl group.

19. The method of claim 1 wherein said plastid gene is rbcL and said ribosome binding site is AGGGAGGGA.

20. The transformed plant of claim 7 wherein said plastid gene is rbcL and said ribosome binding site is AGGGAGGGA.

21. The process of claim 13 wherein said plastid gene is rbcL and said ribosome binding site is AGGGAGGGA.

22. The process of claim 1 wherein the operon comprises 2–4 genes of interest.

23. The process of claim 22, wherein the operon comprises a polyester synthase gene.

24. The process of claim 23 wherein the polyester synthase gene is poly-3-hydroxybutyrate synthase gene.

25. The process of claim 1, wherein the operon comprises a polyester synthase gene.

26. The process of claim 25, wherein the polyester synthase gene is poly-3-hydroxybutyrate synthase gene.

* * * * *